US012626806B1

(12) United States Patent
Wang

(10) Patent No.: US 12,626,806 B1
(45) Date of Patent: May 12, 2026

(54) MEDICAL EXAM PRE-PUSHING SYSTEM AND METHOD

(71) Applicant: Apollo Assets Group, LLC, Clearwater, FL (US)

(72) Inventor: Xiaoyi Wang, Clearwater, FL (US)

( * ) Notice: Subject to any disclaimer, the term of this patent is extended or adjusted under 35 U.S.C. 154(b) by 0 days.

(21) Appl. No.: 19/307,647

(22) Filed: Aug. 22, 2025

(51) Int. Cl.
*G16H 30/20* (2018.01)
*G16H 10/60* (2018.01)
*G16H 30/40* (2018.01)
*G16H 40/40* (2018.01)
*G16H 50/70* (2018.01)

(52) U.S. Cl.
CPC ............. *G16H 30/20* (2018.01); *G16H 10/60* (2018.01); *G16H 30/40* (2018.01); *G16H 40/40* (2018.01); *G16H 50/70* (2018.01)

(58) Field of Classification Search
None
See application file for complete search history.

(56) References Cited

U.S. PATENT DOCUMENTS

| | | | | |
|---|---|---|---|---|
| 5,469,353 A | * | 11/1995 | Pinsky | G16H 30/20 707/999.001 |
| 6,574,629 B1 | * | 6/2003 | Cooke, Jr. | G16H 30/20 |
| 9,495,604 B1 | * | 11/2016 | Fram | G16H 30/20 |
| 2006/0251975 A1 | * | 11/2006 | Taranath | G16H 30/20 430/7 |
| 2008/0140723 A1 | * | 6/2008 | Hernandez | G16H 30/20 |

(Continued)

FOREIGN PATENT DOCUMENTS

CN      111640488 A  *  9/2020  .......... G06F 16/172

OTHER PUBLICATIONS

Rioux, Performance Evaluation of a Picture Archiving and Communications System, Mar. 2001, McGill University Thesis (Year: 2001).*

(Continued)

*Primary Examiner* — Karen A Hranek
(74) *Attorney, Agent, or Firm* — Distinct Patent Law; Justin P. Miller

(57) ABSTRACT

The medical exam pre-pushing system and method proactively distributes medical imaging data from a long-term archive system to multiple PACS. It revolutionizes how historical image data can be transferred proactively from long-term archive to PACS. The system monitors upcoming medical examinations through a hospital information system or electronic medical record interface and identifies patients requiring access to prior imaging studies. The archive system proactively transmits relevant historical imaging data to designated receiving PACS before clinical need arises. The system implements two optimized transmission methods: multi-threaded DICOM Send operations that eliminate resource-intensive query components, and multi-threaded direct file transfer using SMB/CIFS protocol that bypasses DICOM layers entirely for high-volume transfers. This proactive, archive-driven approach improves data transfer speed by a factor of double-digit or even triple-digit, eliminates duplicate query requests from multiple PACS sources, reduces network traffic, and ensures immediate availability of prior studies for clinical comparison purposes.

19 Claims, 8 Drawing Sheets

(56) References Cited

U.S. PATENT DOCUMENTS

| 2008/0253693 | A1* | 10/2008 | Chu | ........................ | G16H 30/20 |
| | | | | | 382/128 |
| 2011/0258288 | A1* | 10/2011 | Dekel | .................... | G16H 30/20 |
| | | | | | 709/217 |
| 2013/0151286 | A1* | 6/2013 | Kablotsky | .............. | G06Q 10/10 |
| | | | | | 715/765 |
| 2019/0304610 | A1* | 10/2019 | Shiibashi | ................ | G06F 16/27 |
| 2020/0202997 | A1* | 6/2020 | Hadad | .................... | H04L 9/0891 |
| 2020/0312439 | A1* | 10/2020 | Kibble | .................... | G16H 10/60 |
| 2024/0427517 | A1* | 12/2024 | Aoki | .................... | H04N 1/2104 |
| 2025/0022585 | A1* | 1/2025 | Sawyer | .............. | H04L 63/0428 |

OTHER PUBLICATIONS

Ferreira, Handling Data Access Latency in Distributed Medical Imaging Environments, 2015, Universidade de Aveiro Thesis (Year: 2015).*

* cited by examiner

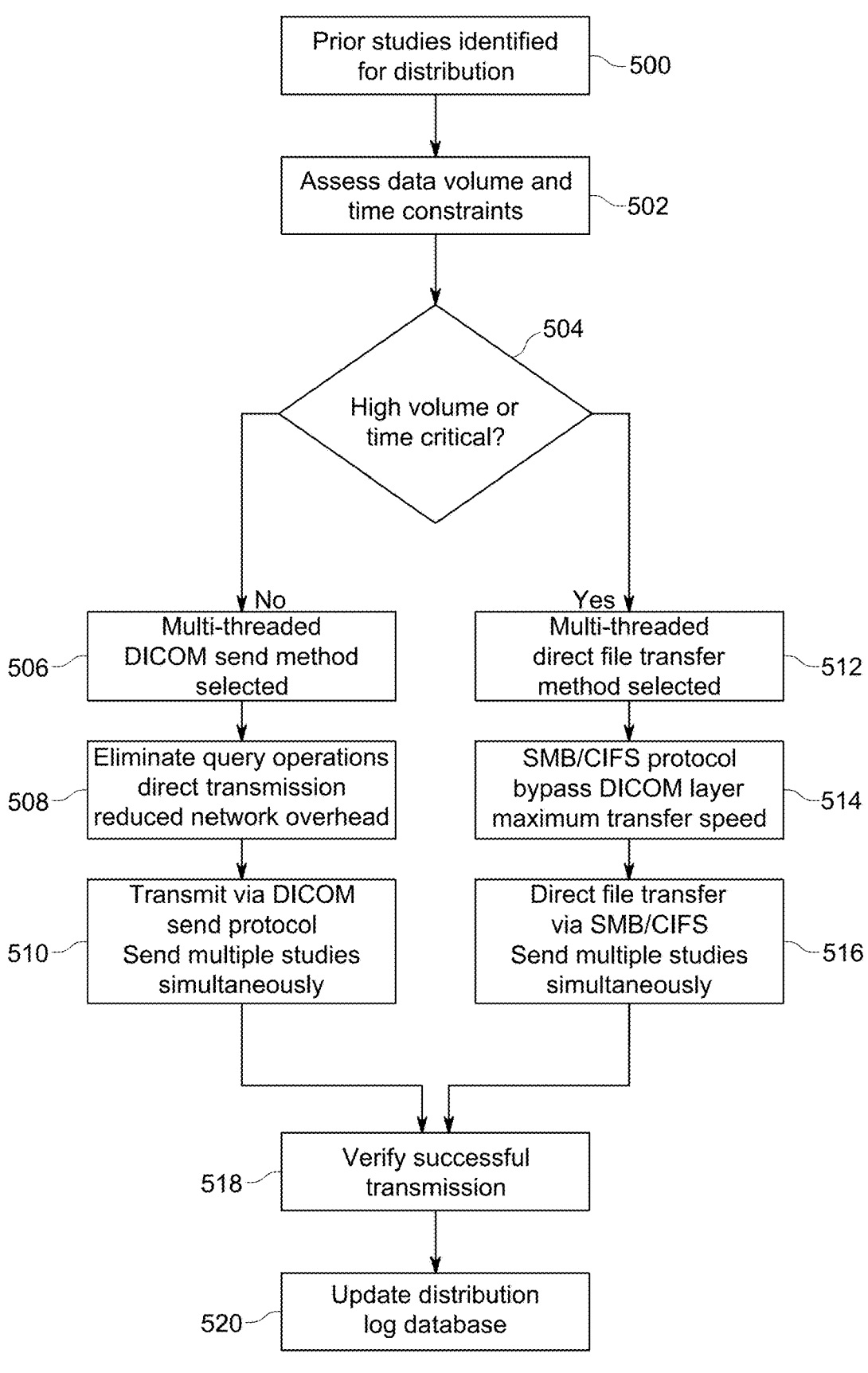

Prior studies identified for distribution —500

Assess data volume and time constraints —502

504
High volume or time critical?

No
Multi-threaded DICOM send method selected 506

Eliminate query operations direct transmission reduced network overhead 508

Transmit via DICOM send protocol Send multiple studies simultaneously 510

Yes
Multi-threaded direct file transfer method selected —512

SMB/CIFS protocol bypass DICOM layer maximum transfer speed —514

Direct file transfer via SMB/CIFS Send multiple studies simultaneously —516

518— Verify successful transmission

520— Update distribution log database

FIG. 3

| Process element | Traditional DICOM pre-fetch | Medical exam pre-pushing system |
|---|---|---|
| Trigger event 600 | Clinician requests prior studies or new examination arrives at PACS 602 | Scheduled examination detected in hospital information system or EMR 604 |
| Initiation 606 | PACS queries long-term archive system 608 | Archive system initiates proactive push operation 610 |
| Query process 612 | Multiple nodes send duplicate query requests 614 | Single coordinated search operation from archive 616 |
| Data retrieval 618 | Single-threaded DICOM Query/Retrieve operations (query component + retrieve component) One study gets processed at a time. 620 | Multi-threaded DICOM Send (eliminate query) or direct file transfer method Multiple studies get processed at the same time. 622 |
| Network impact 624 | High network load from multiple redundant query/retrieve operations 626 | Low network load from coordinated single distribution per study 628 |
| Timing 630 | Reactive approach - after clinical need identified 632 | Proactive approach - before clinical need arises 634 |

FIG. 4

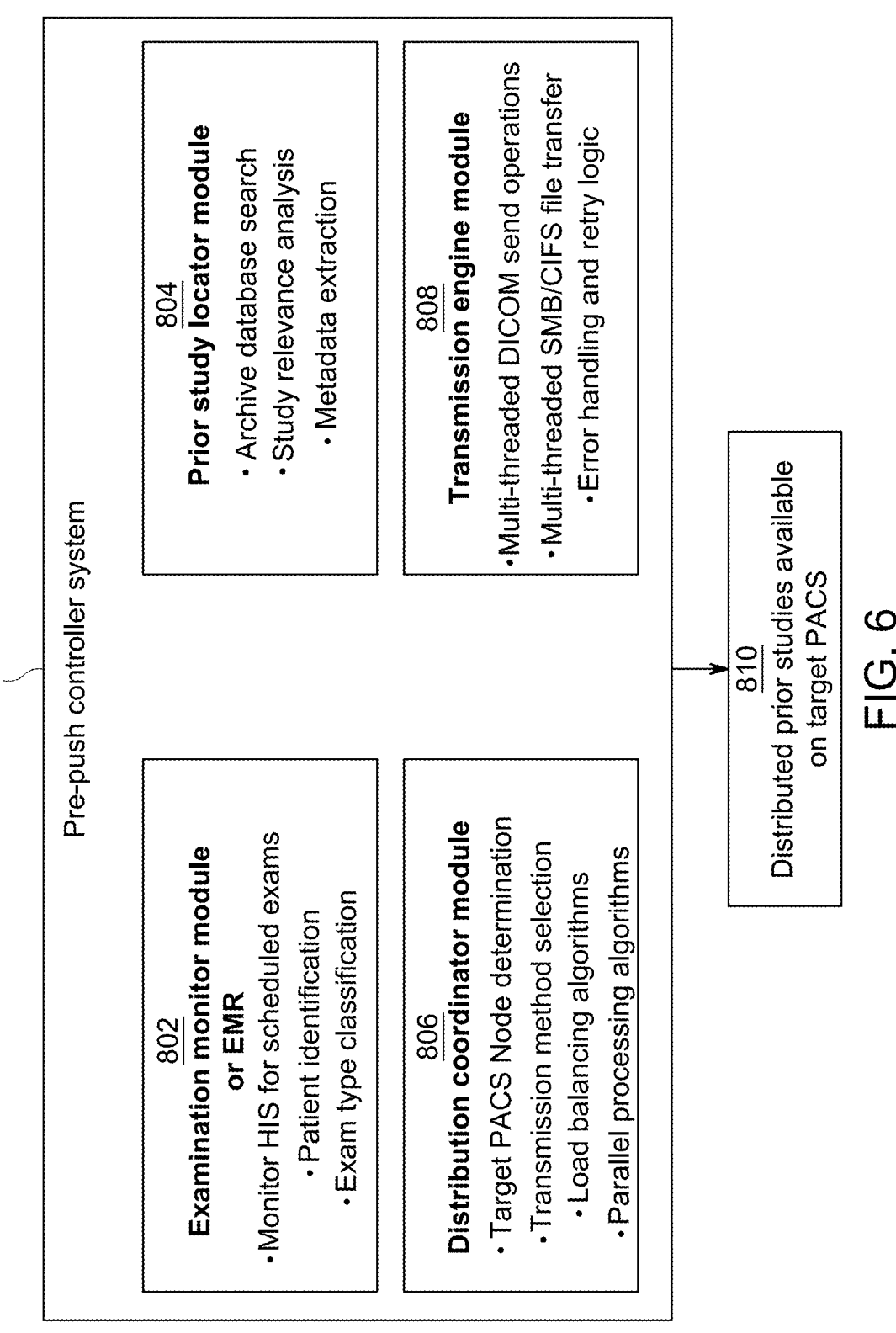

800

Pre-push controller system

802
Examination monitor module or EMR
• Monitor HIS for scheduled exams
• Patient identification
• Exam type classification

804
Prior study locator module
• Archive database search
• Study relevance analysis
• Metadata extraction

806
Distribution coordinator module
• Target PACS Node determination
• Transmission method selection
• Load balancing algorithms
• Parallel processing algorithms

808
Transmission engine module
• Multi-threaded DICOM send operations
• Multi-threaded SMB/CIFS file transfer
• Error handling and retry logic

810
Distributed prior studies available on target PACS

FIG. 6

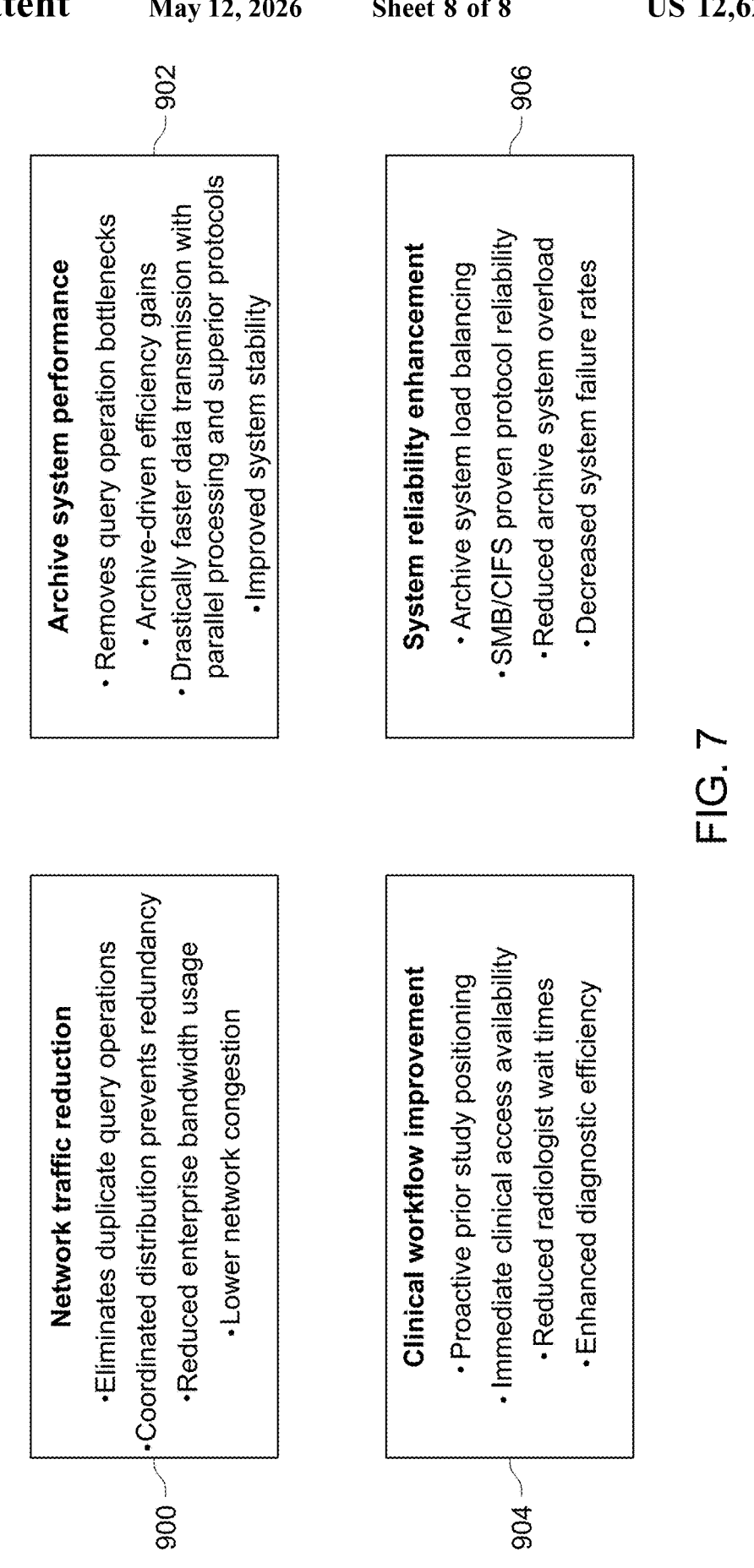

Archive system performance
- Removes query operation bottlenecks
- Archive-driven efficiency gains
- Drastically faster data transmission with parallel processing and superior protocols
- Improved system stability

902

System reliability enhancement
- Archive system load balancing
- SMB/CIFS proven protocol reliability
- Reduced archive system overload
- Decreased system failure rates

906

Network traffic reduction
- Eliminates duplicate query operations
- Coordinated distribution prevents redundancy
- Reduced enterprise bandwidth usage
- Lower network congestion

900

Clinical workflow improvement
- Proactive prior study positioning
- Immediate clinical access availability
- Reduced radiologist wait times
- Enhanced diagnostic efficiency

MEDICAL EXAM PRE-PUSHING SYSTEM AND METHOD

FIELD

The invention relates generally to medical imaging data management systems and methods. More particularly, the invention relates to systems and methods for proactively distributing prior patient imaging studies from long-term archive systems, also known as Vendor Neutral Archive (VNA), to Picture Archiving and Communication Systems (PACS).

BACKGROUND

Modern medical imaging relies on digital Picture Archiving and Communication Systems (PACS) to store, distribute, and display radiological images. When clinicians interpret current patient exams, they often need access to prior studies for comparison purposes. This comparison capability proves essential for tracking disease progression, treatment response, and diagnostic accuracy.

PACS and standalone radiology workstations face inherent storage capacity limitations. To ensure optimal system performance, these systems regularly purge older exams, transferring the exams to separate long-term archive devices with larger storage. The purpose of doing so is to limit the database and storage size, primarily to maximize database response time, and secondarily to reduce costs for high performance storage media. This archival approach creates a two-tier storage system where recent studies remain readily accessible with the fastest access speed possible while historical studies require retrieval from archives.

The current industry standard practice is to use either DICOM (Digital Imaging and Communication in Medicine) Query/Retrieve to manually retrieve historical data from archive back to PACS, or use DICOM pre-fetch to perform more automated retrieval of historic data. There is nothing wrong with the manual method, except that it is manual. Therefore, it is not normally done unless it is absolutely necessary to have historical data in PACS in order to achieve accurate diagnosis. DICOM pre-fetch is an automated way to perform query/retrieve. But there are fatal flaws in DICOM pre-fetch. The most fatal one is its poor performance, because of the DICOM Query/Retrieve protocol it is based on. In its core, DICOM query/retrieve was designed for manually querying a remote DICOM database and then retrieving the desired data from the remote database. The query/retrieve protocol is designed to handle one request at a time. Although this approach works for a small number of requests, for a large institution with large patient volume desiring multiple years' historic data for each patient, it is simply not feasible to handle the large volume of requests and data transfer in a timely manner, and the burden created on the archive system and the volume of network traffic generated can easily cripple the archive system and the enterprise network. This is because DICOM query/retrieve is a very system and network resource intensive operation. As a result, DICOM pre-fetch has very little practical value except for small patient volume applications, such as a few patients a day. This is especially true if DICOM pre-fetch is to be performed over a slow wide-area-network (WAN).

To overcome the inherent limitations and shortcomings of DICOM pre-fetch, a paradigm shift is required. A new design is needed that does not depend on DICOM query/ retrieve, and is capable of distributing large volume of data very rapidly in a limited time window. Thus was born this invention of the medical exam pre-pushing technology, which is archive system driven and is capable of proactively, intelligently, and efficiently distributing large volume of prior medical scans to multiple PACS destinations based on future appointments, with minimal performance impact on the archive system and enterprise network. Its AI driven parallel processing achieves performance gain in data transmission by a factor of double-digit or even triple-digit, compared to standard DICOM pre-fetch.

The disclosed medical exam pre-pushing technology is a revolution in medical imaging data management that addresses the inherent limitations of traditional DICOM pre-fetch approaches while maintaining full compatibility with existing long-term archive/VNA and PACS infrastructures.

SUMMARY

The medical exam pre-pushing system and method represents a paradigm shift in medical imaging data management, moving from reactive and inefficient pre-fetch operations to high performance proactive data distribution. Rather than waiting for individual PACS to request prior patient exams, the medical exam pre-pushing system and method operates from the archive system level, anticipating clinical needs and pushing relevant prior studies to appropriate destinations before they are requested. Above all, the medical exam pre-pushing system and method's ability to distribute large volume of data in a short timeframe is so unique in the industry that no existing technology or methodology can match.

The medical imaging industry has established DICOM (Digital Imaging and Communication in Medicine) pre-fetch as the standard practice for making prior exams available to clinicians. In conventional DICOM pre-fetch operations, PACS query long-term archives to locate prior exams for specific patients, typically triggered by radiology orders or receipt of new patient images. When prior exams are found, the PACS requests the archive to transmit the desired studies using the standard DICOM Query/Retrieve process.

The fundamental flaw with DICOM pre-fetch is that DICOM Query/Retrieve can only request one study at a time and then receive associated images one by one. In a large patient volume environment, it is simply not feasible to pre-fetch multiple studies spanned over multiple years for each patient within a reasonable time window. This is due to the fact that DICOM Query/Retrieve protocol was designed and intended for limited, ad hoc operations performed on demand and was never intended for automated movement of large volume of data. Additionally, this reactive approach creates other significant technical challenges. When multiple PACS nodes simultaneously request multiple prior exams for numerous patients, the resulting volume of query and retrieve operations can overwhelm archive systems and cripple enterprise networks. The query/retrieve operations prove to be very resource-intensive, creating performance bottlenecks that affect overall system responsiveness.

These performance limitations have led many long-term archive systems to disallow DICOM pre-fetch functionality entirely, forcing clinicians to manually request prior studies or proceed without historical comparison data. This situation compromises clinical workflow efficiency and may impact diagnostic quality, particularly in cases where prior study comparison is medically necessary, such as in diagnostic imaging for oncology.

The archive-driven approach disclosed addresses the poor performance, network congestion and duplicate request problems inherent in conventional DICOM pre-fetch systems. By centralizing the decision-making process at the archive level and utilizing highly efficient parallel processing, the medical exam pre-pushing system and method coordinates data distribution across multiple PACS, distributing multiple studies simultaneously, and eliminating redundant requests for the same patient data. For example, when multiple radiologists need access to the same patient's prior cardiac studies, the system can push those studies a single time to each required destination rather than processing separate query and retrieve requests from each location, and many studies can be transmitted simultaneously.

The medical exam pre-pushing system and method implements two distinct data transmission methods optimized for different performance requirements. The first method utilizes multi-threaded DICOM Send operations, which provide significant performance gain over conventional DICOM Query/Retrieve by sending multiple studies simultaneously and eliminating the resource-intensive query component. This approach directly transmits identified prior exams without requiring preliminary database searches, reducing both network traffic and processing overhead, and improving the performance by a factor of the thread count. For example, if there are 10 threads running with each thread responsible for sending a study, then the performance improvement would be at least a factor of 10.

For scenarios requiring even higher performance, such as when multiple years of prior studies must be transferred to multiple PACS destinations within limited time windows, the medical exam pre-pushing system and method employs multi-threaded direct DICOM data file transfer using Microsoft's SMB/CIFS protocol. This approach bypasses the DICOM protocol layer entirely, utilizing the native Windows file transfer protocol to achieve maximum transfer speeds. The SMB/CIFS protocol provides exceptional reliability and performance that exceeds DICOM-based transfer methods. With this option, data transfer that would otherwise require hours to query and retrieve with standard DICOM query/retrieve could be easily completed in a matter of minutes.

This proactive distribution model ensures that clinicians have immediate access to relevant prior studies when interpreting current exams, eliminating delays associated with archive retrieval requests. This capability proves particularly valuable for time-sensitive clinical scenarios, such as emergency radiology interpretations or interventional procedure planning, where rapid access to historical imaging data can impact patient care decisions.

Imaging types that the system and method can transfer and index include, but not limited to, computed tomography (CT), magnetic resonance imaging (MRI), positron emission tomography (PET), ultrasound (US), nuclear medicine (NM), digital X-Ray (CR/DR), mammogram (MG), X-Ray Angiography (XA), radiotherapy dose/image/plan, etc.

The system runs in a long-term archive environment that contains archived medical imaging studies stored in DICOM (Digital Imaging and Communications in Medicine) format, providing a repository for historical patient imaging data. A software processor is operatively running in the long-term archive environment to enable data processing and communication functions.

A software processor in the context of this medical exam pre-pushing system refers to a computer program or set of program instructions that, when executed by a hardware processor, performs data processing operations on medical imaging information. The software processor comprises executable code that implements processing logic to analyze, transform, and manage data within the long-term archive environment.

The software processor operates as an intermediary processing layer between the hardware processor and application-level software modules. It executes programmed algorithms that:

Process input data-Receive and interpret scheduling information, patient identifiers, and examination data from external systems;

Execute decision logic-Implement rule-based algorithms to determine distribution requirements and transmission methods;

Transform data formats-Convert between different data representations and protocols (DICOM, SMB/CIFS); and Manage processing threads—Controls parallel processing operations for simultaneous data transmission. The software processor is distinguished from the hardware processor in that it comprises the executable instructions themselves rather than the physical computing device. It functions as a logical processing entity that utilizes the hardware processor's computational resources to perform defined operations on medical imaging data.

In this invention, the software processor specifically enables the pre-push controller functionality by executing the programmed logic that coordinates autonomous monitoring, searching, and distribution operations without requiring external triggers from PACS systems.

The software processor may be implemented as compiled binary code, interpreted scripts, or virtual machine bytecode stored in non-transitory computer-readable media and loaded into system memory for execution by the hardware processor.

The system further includes software modules which, when executed by the processor, implement a pre-push controller.

A software module in the context of this medical exam pre-pushing system comprises computer-executable program instructions stored in computer-readable memory that, when executed by a processor, perform specific functional operations within the long-term archive environment. Each software module represents a discrete functional component that implements defined processes through programmatic logic.

Specifically, the invention includes four primary software modules:

Examination Monitor Module-Program instructions that implement automated polling and data extraction functions to interface with hospital information systems;

Prior Study Locator Module-Program instructions that execute database search algorithms and metadata analysis routines within the archive system;

Distribution Coordinator Module-Program instructions that implement decision logic for target selection and transmission method determination; and Transmission Engine Module-Program instructions that control network communication protocols and execute data transfer operations.

Each software module consists of compiled or interpretable code that the processor executes to transform input data into output actions. The modules may be implemented in any suitable programming language and stored in non-transitory computer-readable storage media accessible to the processor.

The software modules are distinct from mere abstract ideas or mental processes because they comprise specific computer instructions that cause the processor to perform concrete data manipulation and transmission operations that improve the functioning of the medical imaging archive system itself.

The medical exam pre-pushing system and method maintains full compatibility with existing PACS and long-term archive infrastructures while providing these performance enhancements. Archive systems can implement the technology without requiring modifications to individual PACS, enabling healthcare facilities to improve their imaging workflow efficiency without major system overhauls.

BRIEF DESCRIPTION OF THE DRAWINGS

The invention can be best understood by those having ordinary skill in the art by reference to the following detailed description when considered in conjunction with the accompanying drawings in which:

FIG. 3 is a flowchart illustrating the data transmission method selection process, showing the decision logic for choosing between the enhanced multi-threaded DICOM Send operations and multi-threaded direct file transfer based on data volume and time constraints.

FIG. 4 is a comparison table contrasting the process elements of traditional DICOM pre-fetch operations with the medical exam pre-pushing system and method, highlighting key differences in trigger events, initiation methods, query processes, performance, and network impact.

FIG. 6 is a detailed component diagram of the pre-push controller system, showing the examination monitor module, prior study locator module, distribution coordinator module, and transmission engine module.

FIG. 7 is a summary diagram of the technical performance benefits achieved by the medical exam pre-pushing system and method, including drastically higher performance for data transmission, network traffic reduction, archive system performance improvements, clinical workflow enhancements, and system reliability benefits.

DETAILED DESCRIPTION

Figure 1:
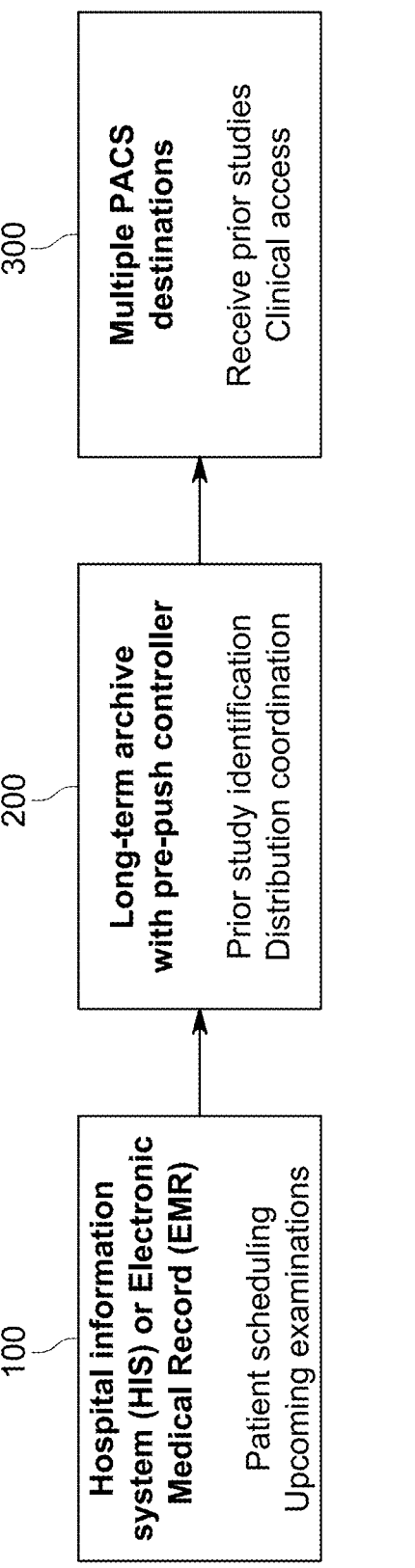
FIG. 1 is a system architecture diagram illustrating the overall components of the medical exam pre-push technology, showing the data flow from the Hospital Information System (HIS) or Electronic Medical Record (EMR) through the long-term archive with pre-push controller to multiple PACS destinations.

Reference will now be made in detail to the presently preferred embodiments of the invention, examples of which are illustrated in the accompanying drawings. Throughout the following detailed description, the same reference numerals refer to the same elements in all figures.

Referring to FIG. 1, the overall system architecture for the medical exam pre-pushing system and method comprises three primary components working in coordinated fashion. The Hospital Information System (HIS) or Electronic Medical Record (EMR) 100 contains patient scheduling information and upcoming examination data. The HIS/EMR 100 maintains records of scheduled medical imaging examinations, including patient identifiers, examination types, scheduled dates and times, ordering physician, and interpreting physician information.

The long-term archive 200 includes archived medical imaging studies and is the host environment for the pre-push controller functionality for autonomous proactive data distribution. The long-term archive 200 stores historical patient imaging studies that have been transferred from PACS. The pre-push controller within long-term archive 200 autonomously monitors the HIS/EMR 100 for upcoming examinations and independently determines and executes distribution of relevant prior studies without requiring a request from a PACS. In subsequent discussions, long-term archive implies long-term archive with the pre-push controller integrated.

Multiple PACS 300 serve as passive destinations for archive-initiated data distribution. These PACS destinations 300 provide clinical access points where radiologists, referring physicians, and other clinicians review current and prior imaging studies for diagnostic purposes. The PACS destinations 300 do not initiate any requests for prior studies. Instead, they passively receive studies pushed by long-term archive 200, fundamentally eliminating the traditional query/retrieve workflow.

Figure 2:
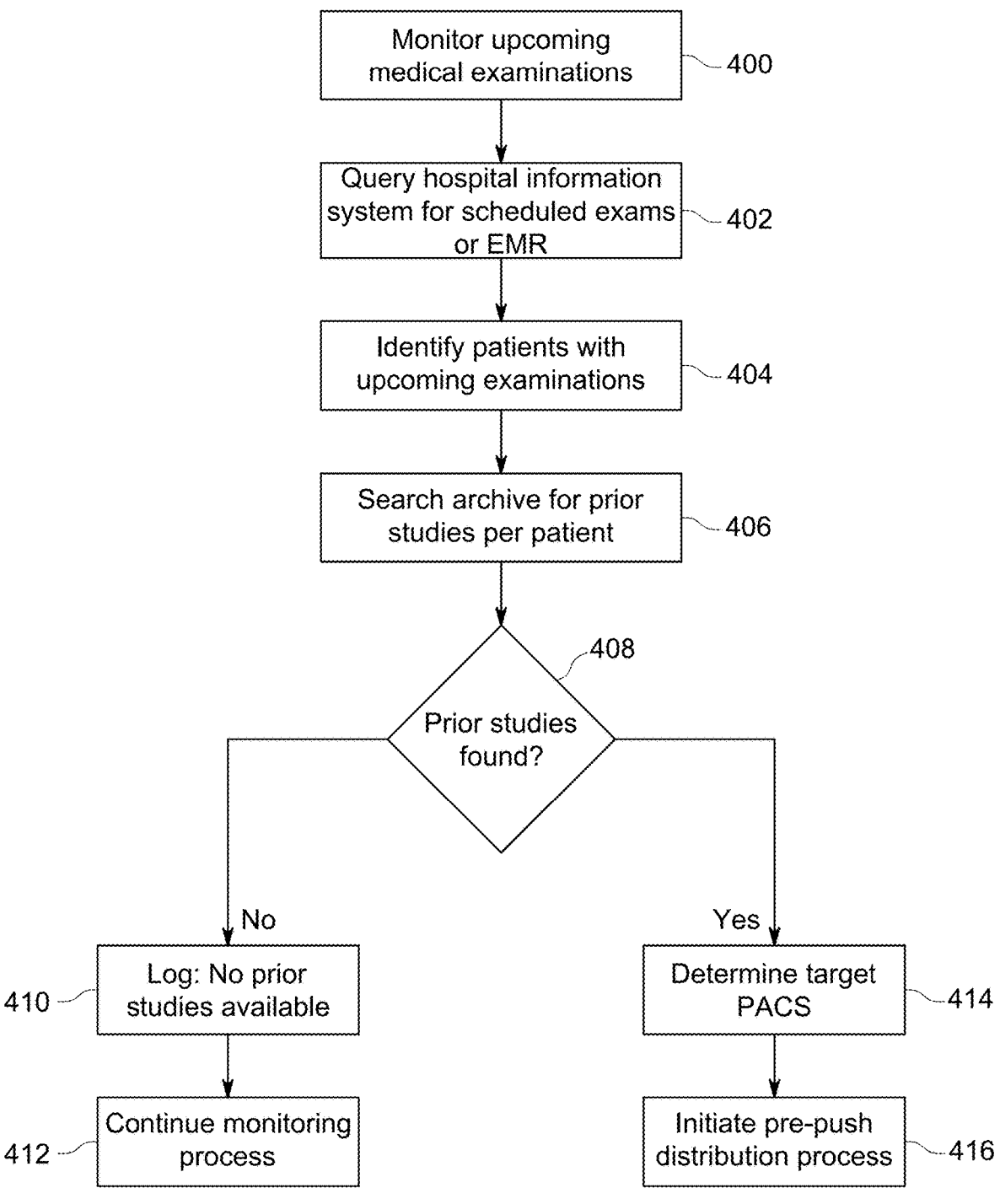
FIG. 2 is a flowchart depicting the main pre-push process, including the steps of monitoring upcoming examinations, identifying patients, searching for prior studies, and initiating proactive distribution based on study availability.

The archive-initiated pre-push process, illustrated in FIG. 2, begins with monitoring operation 400 that continuously surveys upcoming medical examinations through autonomous polling of HIS/EMR 100 (see FIG. 1). This monitoring process 400 operates independently from any PACS activity and interfaces solely with HIS/EMR 100 to identify scheduled imaging studies that may require access to historical patient data for comparison purposes.

Query operation 402 retrieves scheduled examination information from HIS/EMR 100 using archive-controlled polling intervals ranging from, for example, 15 minutes to 24 hours, based on institutional workflow patterns. This operation 402 obtains patient identifiers, examination types, scheduled times, anatomical regions, and clinical priority levels necessary for determining which prior studies may be clinically relevant. The query operation 402 operates on a predetermined schedule controlled entirely by long-term archive 200 without any external triggers from PACS.

Patient identification process 404 analyzes the retrieved examination data using archive-maintained algorithms to extract unique patient identifiers and associated clinical information. This process 404 creates a prioritized list of patients with upcoming examinations who may benefit from having their prior studies made available on PACS 300. The prioritization algorithm considers examination urgency (emergency, urgent, routine), examination type (comparison-dependent vs. standalone), and historical access patterns specific to each clinical department.

Archive search operation 406 systematically examines the long-term archive 200 using database queries to locate prior imaging studies associated with each identified patient. This search operation 406 uses patient identifiers, demographic information, examination type, and examination dates to locate relevant historical studies stored in long-term archive 200. The search implements anatomical region matching, modality correlation analysis, and clinical context filtering to identify studies with high likelihood of clinical relevance.

Decision point 408 determines whether clinically relevant prior studies exist in long-term archive 200 for each identified patient. When no relevant prior studies are found, the process follows the "NO" path to logging operation 410, which records the absence of relevant prior studies in the distribution log database, followed by continuation operation 412 that returns to monitoring process 400.

When relevant prior studies are located above the relevance threshold, the process follows the "YES" path to target determination operation 414, which identifies the appropriate PACS destinations 300 (see FIG. 1) that should receive the prior studies. This determination 414 considers examination scheduling location, interpreting physician assignments, PACS storage capacity, current PACS utilization levels, and network bandwidth availability to select optimal target destinations.

Distribution initiation operation 416 begins the autonomous transmission of identified prior studies to the determined target PACS destinations 300. This operation 416 coordinates with the transmission method selection process illustrated in FIG. 3 to optimize data transfer efficiency based on real-time network conditions and data volume requirements.

FIG. 3 illustrates the logic for selecting optimal data transmission methods based on volume and time requirements, with all decisions made autonomously by the long-term archive 200. Prior study identification process 500 provides the input data for transmission method selection, including the number of studies, total data volume, clinical urgency factors, archive system resource availability, and current network utilization metrics.

Assessment operation 502 evaluates data volume and time constraints using archive-maintained algorithms to determine the most appropriate transmission method. This assessment 502 considers factors such as real-time network bandwidth availability, current archive system load, target PACS capacity, clinical scheduling requirements, and historical transmission performance data to optimize transmission decisions.

Decision point 504 determines whether the transmission requirements exceed predetermined thresholds for data volume or time criticality using configurable parameters maintained in long-term archive 200. This decision point 504 uses dynamic thresholds that adapt based on current network conditions, target PACS capabilities, and clinical priority levels.

For standard volume requirements, the process selects enhanced multi-threaded DICOM Send method 506, which provides significant performance increase over traditional DICOM Query/Retrieve operations. Enhanced DICOM Send implementation 508 eliminates the resource-intensive query component entirely, implements parallel transmission streams for multiple studies, and includes enhanced error detection with automatic retry mechanisms. Transmission operation 510 executes the enhanced DICOM Send protocol to transfer prior studies directly to target PACS 300 with transmission speed improvement by a factor of double to triple digits over the conventional DICOM operations.

For high volume requirements or time-critical scenarios, the process selects direct file transfer method 512. This approach 514 utilizes multi-threaded SMB/CIFS protocol with custom DICOM metadata header insertion to bypass the DICOM protocol layer entirely while maintaining full metadata integrity. File transfer operation 516 implements the multi-threaded SMB/CIFS protocol with custom headers for direct transfer of DICOM data files, achieving transmission speed improvement by triple-digit factors compared to standard DICOM pre-fetch operations.

Verification operation 518 confirms successful transmission using checksum validation, file integrity verification, and destination confirmation protocols, which can include one or more messages. This verification 518 includes MD5 hash validation, DICOM metadata integrity checks, and target system acknowledgment confirmation. Update operation 520 maintains a comprehensive distribution log database that tracks successful transmissions, performance metrics, and provides audit capabilities for regulatory compliance.

FIG. 4 provides a detailed comparison between traditional DICOM pre-fetch operations and the medical exam pre-pushing system and method across six critical process elements. This comparison demonstrates the fundamental differences in approach and the technical advantages achieved by the invention through multi-threaded archive-initiated autonomous operation.

Trigger event comparison 600 shows that traditional systems 602 react to clinician requests or new examination arrivals initiated by PACS, while the medical exam pre-pushing system and method 604 proactively responds to scheduled examinations detected through autonomous polling of HIS/EMR 100 by long-term archive 200. This archive-initiated approach eliminates delays associated with PACS-reactive systems and ensures prior studies are available before clinical need arises.

Initiation process comparison 606 illustrates that traditional systems 608 require individual PACS to initiate queries to the long-term archive, while the medical exam pre-pushing system and method 610 centralizes all initiation at the long-term archive level with complete autonomy from PACS activity. This archive-controlled approach eliminates all PACS-initiated operations and provides completely autonomous distribution control.

Query process comparison 612 demonstrates that traditional systems 614 generate multiple duplicate queries from different PACS destinations requesting identical patient data, while the medical exam pre-pushing system and method 616 performs a single coordinated search operation initiated and controlled entirely by long-term archive 200 (see FIG. 1).

This reduction in query operations eliminates PACS-generated network traffic and archive system processing load.

Data retrieval comparison 618 shows that traditional systems 620 use resource-intensive single-threaded DICOM Query/Retrieve operations initiated by PACS, while the medical exam pre-pushing system and method 622 utilizes multi-threaded archive-initiated enhanced DICOM Send operations or multi-threaded direct file transfer methods controlled exclusively by the long-term archive 200. The elimination of all PACS-initiated query components and the implementation of archive-controlled multi-threaded protocol optimization provide drastic performance improvements. DICOM Query/Retrieve can only request one study at a time and images are received one by one, while the medical exam pre-pushing system and method 622 can send multiple studies and images simultaneously utilizing multi-threading, and the only limiting factors are the availability of network bandwidth and archive system's computer resources.

Network impact comparison 624 illustrates that traditional systems 626 create high network loads through multiple PACS-initiated redundant operations, while the medical exam pre-pushing system and method 628 minimizes network impact through archive-controlled coordinated distribution that operates independently of PACS activity. This reduction in network traffic prevents the enterprise network congestion caused by PACS-initiated pre-fetch requests.

Timing comparison 630 shows that traditional systems 632 operate reactively after clinical need is identified through PACS-initiated requests, while the medical exam pre-pushing system and method 634 operates proactively through archive-controlled monitoring before clinical need arises. This timing advantage ensures immediate availability of prior studies when clinicians require them for diagnostic purposes without any PACS involvement in the distribution process.

Figure 5A:
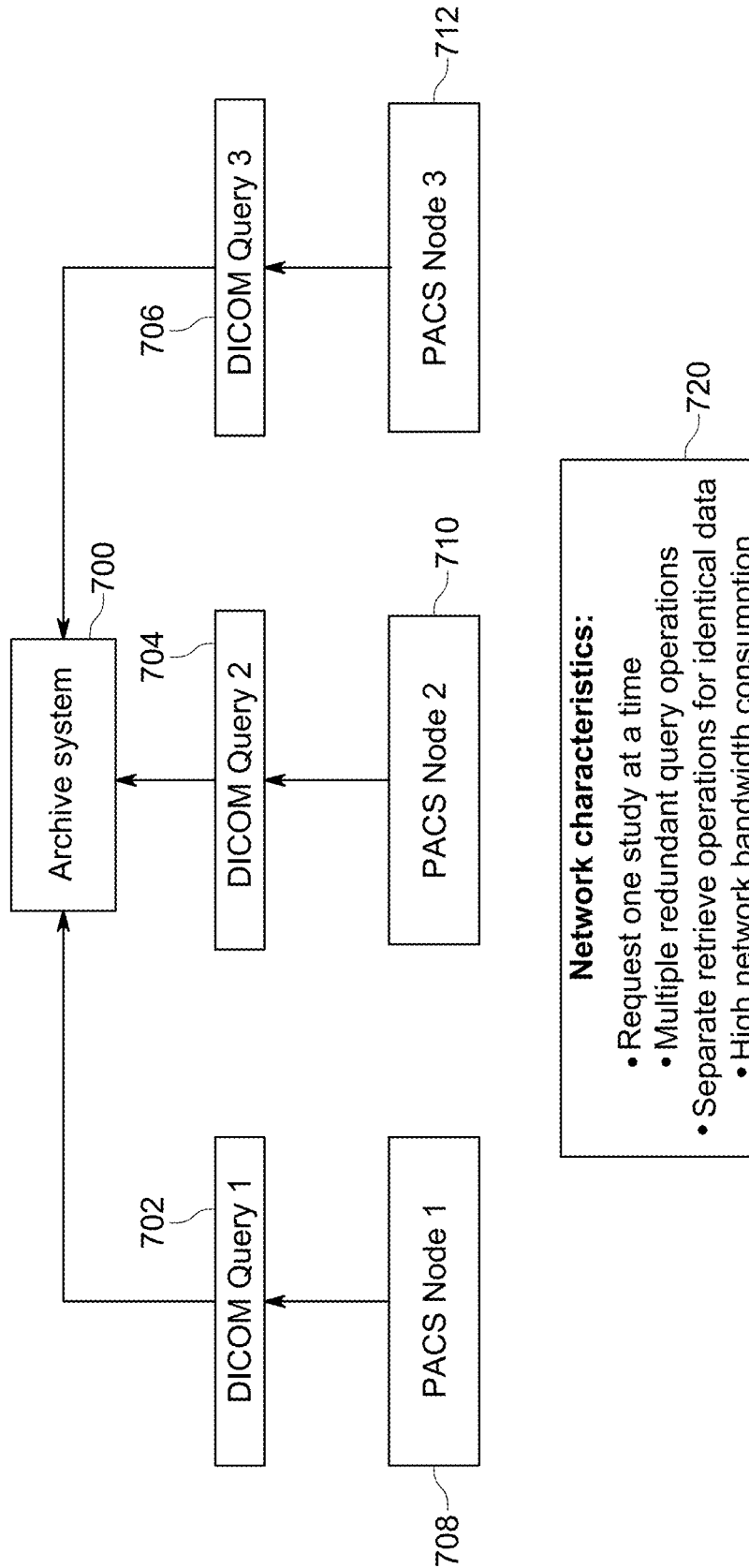
FIG. 5A is a network traffic flow diagram showing the traditional DICOM pre-fetch approach, illustrating multiple redundant query and retrieve operations from separate PACS sources to the archive system.

FIG. 5A illustrates the network traffic patterns characteristic of traditional DICOM pre-fetch operations where PACS initiate all requests, one study at a time. Archive system 700 receives multiple simultaneous query requests 702, 704, 706 from independent PACS nodes 708, 710, 712. Each PACS node independently queries for the same patient data, creating redundant network traffic and archive processing load through PACS-initiated operations.

These redundant PACS-initiated operations consume network bandwidth unnecessarily and create processing bottlenecks at archive system 700. The network characteristics 720 include multiple redundant query operations initiated by PACS nodes, separate retrieve operations for identical data, high network bandwidth consumption from PACS activity, and archive system processing overload from multiple PACS requests.

Figure 5B:
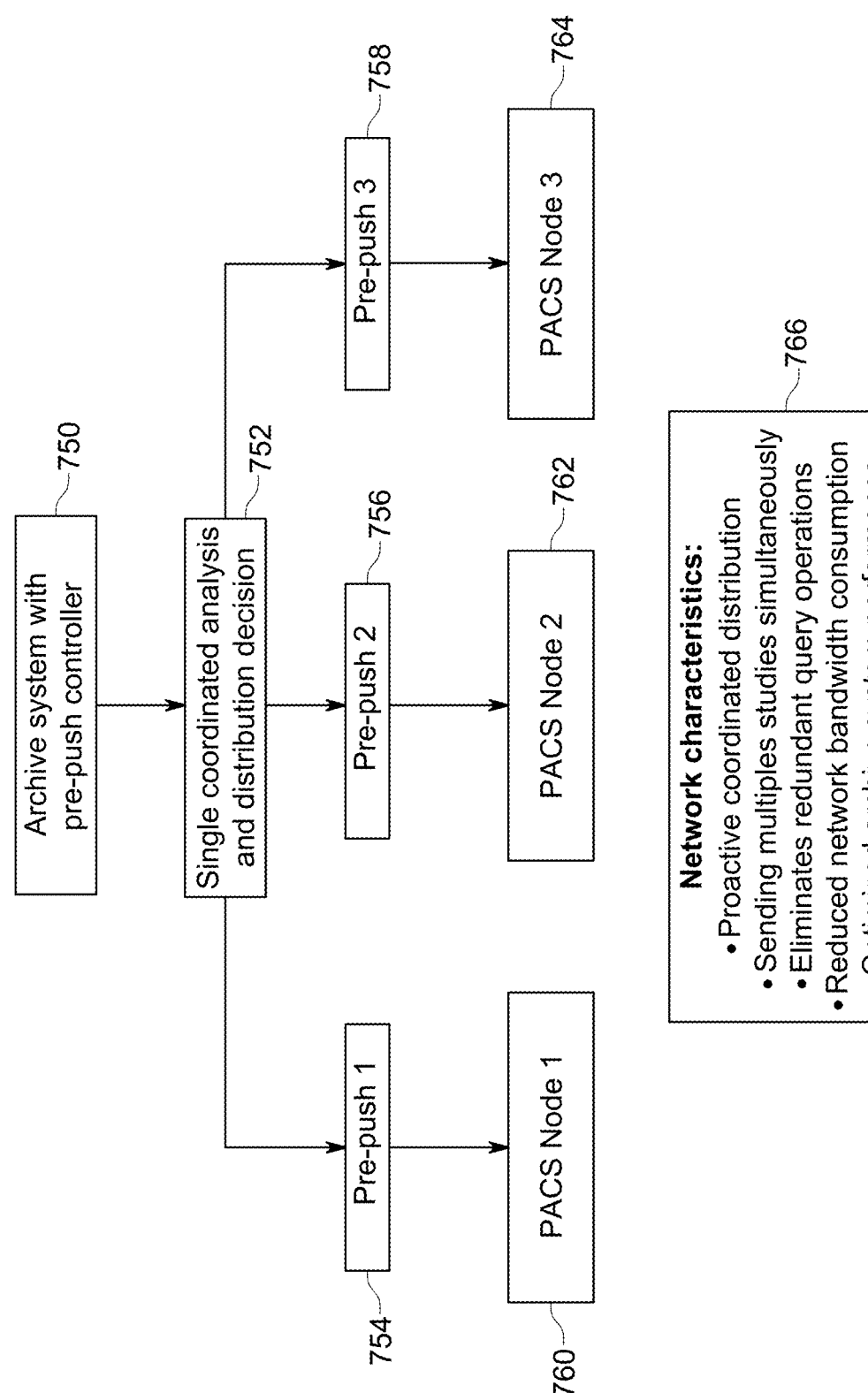
FIG. 5B is a network traffic flow diagram showing the medical exam pre-pushing system and method approach, illustrating coordinated distribution with parallel processing from the archive system with pre-push controller to multiple PACS destinations, increasing data transfer performance and eliminating redundant operations.

FIG. 5B illustrates the optimized network traffic patterns achieved by the medical exam pre-pushing system and method where all operations are initiated by the archive system. Archive system 750 with integrated pre-push controller performs a single coordinated analysis 752 to determine distribution requirements without any input from PACS. This archive-controlled approach eliminates all PACS-initiated query operations and coordinates data distribution efficiently through autonomous archive operation.

Archive-initiated pre-push operations 754, 756, 758 distribute prior studies to PACS nodes 760, 762, 764 through coordinated transmission controlled entirely by archive system 750 rather than through PACS-initiated individual operations. Multiple studies can be pushed to a destination simultaneously. The network characteristics 766 include archive-initiated coordinated distribution, complete elimination of PACS-generated query operations, reduced network bandwidth consumption through archive control, and optimized archive system performance through multi-threaded autonomous operation.

FIG. 6 provides detailed component architecture for pre-push controller system 800 implemented within long-term archive 200 (see FIG. 1). The pre-push controller system 800 comprises four primary modules that work together to implement multi-threaded autonomous proactive distribution functionality without requiring any input from PACS.

Examination Monitor Module 802 autonomously interfaces with HIS/EMR 100 (see FIG. 1) to monitor scheduled examinations, identify patients, and classify examination types without receiving any requests from PACS. This Examination Monitor Module 802 maintains continuous awareness of upcoming clinical activities that may require prior study access and autonomously triggers appropriate distribution actions based on archive-controlled algorithms.

Prior Study Locator Module 804 performs autonomous archive database searches, analyzes study relevance using machine learning algorithms, and extracts metadata necessary for distribution decisions without any PACS involvement. This Prior Study Locator Module 804 uses patient identifiers, anatomical region correlation matrices, and clinical relevance scoring to locate relevant historical imaging studies within long-term archive 200 through completely autonomous operation.

Distribution Coordinator Module 806 autonomously determines target PACS, selects optimal transmission methods, and implements load balancing and multi-threading algorithms to optimize system performance without receiving any specifications from PACS. This Distribution Coordinator Module 806 coordinates all distribution activities to prevent system overload and ensure efficient resource utilization through archive-controlled optimization algorithms.

Transmission Engine Module 808 autonomously executes multi-threaded enhanced DICOM Send operations, implements multi-threaded SMB/CIFS file transfer with custom headers, and provides error handling and retry logic for reliable data transmission without requiring any PACS interaction. This Transmission Engine Module 808 adapts transmission methods based on archive-analyzed system conditions and requirements to ensure successful prior study delivery through completely autonomous operation.

The coordinated autonomous operation of these modules 802, 804, 806, 808 results in distributed prior studies 810 being available on target PACS before clinical need arises, enabling immediate access for diagnostic purposes through completely archive-controlled proactive positioning.

FIG. 7 summarizes the technical performance benefits achieved through implementation of the medical exam pre-pushing system and method across four critical areas of system operation.

Network Traffic Reductions 900 include elimination of duplicate query operations, coordinated distribution to prevent redundancy, reduction in enterprise bandwidth usage, and lower overall network congestion. These improvements address the fundamental network limitations that often disable traditional DICOM pre-fetch functionality.

Archive System Performance 902 improvements include removal of Query operation bottlenecks, providing archive-driven efficiency gains, enabling drastically faster data transmission with superior protocols and parallel processing, and improving system stability. These enhancements allow archive systems to maintain pre-fetch functionality with unmatched performance.

Clinical Workflow Improvements 904 include proactive prior study positioning, ensuring immediate clinical access availability, reducing radiologist wait times, and enhancing diagnostic efficiency. These benefits directly impact patient care quality and clinical productivity.

System Reliability Enhancements 906 include archive system load balancing, utilizing SMB/CIFS proven protocol reliability, reducing archive system overload, and decreasing system failure rates. These improvements ensure consistent system availability and reliable prior study access.

The medical exam pre-pushing system and method is a revolution in medical imaging data management that addresses the inherent limitations of traditional DICOM pre-fetch approaches while maintaining full compatibility with existing long-term archive and PACS infrastructures. The proactive, archive-driven approach drastically improves data transfer speed through parallel processing, eliminates network congestion and system overload issues while providing superior clinical workflow efficiency through predictive prior study positioning.

Equivalent elements can be substituted for the ones set forth above such that they perform in substantially the same manner in substantially the same way for achieving substantially the same result.

What is claimed is:

1. A method for improving medical imaging archive management by proactively distributing medical imaging data from a long-term archive system to multiple Picture Archiving and Communication Systems (PACS), the method comprising:

automatically monitoring, by the long-term archive system, a hospital information system (HIS) or electronic medical record (EMR) database to identify patients with upcoming medical imaging examinations scheduled within a configurable time window;

for each identified patient, searching the long-term archive system using patient identifiers to locate prior medical imaging studies stored in the long-term archive system;

when prior medical imaging studies are located, automatically determining target PACS based on examination scheduling data and PACS matching criteria;

selecting, by the long-term archive system, an optimized data transmission protocol from a group consisting of: (i) multi-threaded DICOM Send operations that eliminate DICOM Query components to reduce network processing overhead, and (ii) multi-threaded direct file transfer operations using SMB/CIFS protocol that bypass DICOM protocol layers entirely;

proactively transmitting the prior medical imaging studies from the long-term archive system to the target PACS using the optimized data transmission protocol with parallel processing before receiving requests from the target PACS; and maintaining, by the long-term archive system, a distribution log database that tracks successful transmissions and prevents duplicate distribution operations;

wherein proactive transmission with parallel processing increases data transfer speed to ensure constant availability of prior studies in PACS and eliminates network congestion caused by multiple simultaneous DICOM Query/Retrieve requests and improves archive system performance by coordinating data distribution to prevent redundant processing loads;

wherein automatically determining target PACS comprises:

parsing the examination scheduling data, by the long-term archive system, to identify an examination location;

querying, by the long-term archive system, a PACS registry database to identify PACS associated with an ordering physician, examination location, and interpreting physician; and checking availability status of the target PACS; and selecting available PACS with sufficient storage capacity for the prior medical imaging studies, without requiring input from the PACS.

2. The method of claim 1, wherein the configurable time window is between 1 hour to 30 days before a scheduled examination time.

3. The method of claim 1, wherein selecting the optimized data transmission protocol comprises:

calculating, by the long-term archive system, total data volume for the prior medical imaging studies to be transmitted;

when the total data volume equals or exceeds a predetermined threshold, selecting the multi-threaded direct file transfer operations using SMB/CIFS protocol; and when the total data volume is less than the predetermined threshold, selecting the multi-threaded DICOM Send operations;

whereby an optimal threshold is determined based on a network and archive system environment.

4. The method of claim 1, wherein the prior medical imaging studies comprise studies from multiple imaging modalities including, but not limited to, computed tomography (CT), magnetic resonance imaging (MRI), positron emission tomography (PET), ultrasound (US), nuclear medicine (NM), digital X-Ray (CR/DR), mammogram (MG), X-Ray Angiography (XA), and radiotherapy dose/image/plan.

5. The method of claim 1, wherein parallel processing comprises:

a parallel processing algorithm that determines an optimal number of threads to run to transmit data without causing overload to long-term archive system and an enterprise network; and a mechanism to launch multiple threads simultaneously with each thread responsible for transmitting one study;

whereby when compared to a conventional DICOM prefetch, which is based on a request-respond model with studies being requested one by one and an archive system responds to requests one by one, a performance increase is minimally by a factor of a thread count.

6. The method of claim 1, further comprising:

after successful transmission, sending confirmation messages to the target PACS indicating availability of the prior medical imaging studies; and updating the distribution log database with transmission completion timestamps and data integrity verification results.

7. A medical imaging archive system comprising:

a long-term storage device containing archived medical imaging studies in DICOM format;

a hardware or virtual processor operatively running in a long-term archive environment;

software modules that, when executed by the hardware or virtual processor, cause implementation of a pre-push controller comprising:

an examination monitor module configured to interface with a hospital information system or electronic medical record database and automatically identify patients with upcoming medical examinations;

a prior study locator module configured to search the long-term archive environment using patient identifiers and metadata to locate relevant prior medical imaging studies;

a distribution coordinator module configured to determine target PACS based on examination scheduling data by:

parsing the examination scheduling data to identify an examination location;

querying a PACS registry database to identify PACS associated with an ordering physician, the examination location, and an interpreting physician;

checking availability status of the target PACS; and selecting available PACS with sufficient storage capacity for the relevant prior medical imaging studies, without requiring input from the PACS, and select transmission methods based on data volume thresholds and network bandwidth availability; and a transmission engine module configured to execute either: (i) multi-threaded DICOM Send operations that eliminate query processing steps, or (ii) multi-threaded direct SMB/CIFS file transfer operations that bypass DICOM protocol overhead;

a network interface configured to proactively transmit multiple prior medical imaging studies simultaneously to multiple destination PACS before receiving distribution requests;

wherein the pre-push controller coordinates data distribution operations to eliminate duplicate network requests from multiple PACS and reduces archive system processing load through centralized distribution management.

8. The medical imaging archive system of claim 7, wherein the examination monitor module is configured to query the hospital information system or EMR database at configurable intervals.

9. The medical imaging archive system of claim 7, wherein the distribution coordinator module comprises:

a registry database storing PACS network addresses and capacity specifications;

a load balancing algorithm configured to distribute transmission tasks across multiple target PACS based on current PACS utilization levels;

a parallel processing algorithm that calculates a maximum number of threads to run to achieve a highest data transmission speed possible without impacting enterprise network and archive system performance; and a multi-thread launching mechanism to launch multiple data transmission thread with each one responsible for transmitting one study.

10. The medical imaging archive system of claim 7, wherein the transmission engine module is configured to:

establish secure network connections using Transport Layer Security (TLS) encryption for data transmission;

perform data integrity verification using checksum algorithms during transmission; and implement automatic retry logic for failed transmission attempts.

11. The medical imaging archive system of claim 7, further comprising a user interface module configured to:

display real-time status of proactive transmission operations;

provide administrative controls for configuring transmission schedules and data retention policies;

generate reports of system performance metrics including network bandwidth utilization, archive system load, and transmission success rates.

12. The medical imaging archive system of claim 7, wherein the prior study locator module is configured to:

analyze examination type metadata to identify anatomically relevant prior studies;

apply configurable filters based on study age, imaging modality, and clinical relevance scores; and rank located prior studies by clinical importance for transmission prioritization.

13. An archive-initiated method for increasing data transmission speed and optimizing network performance in medical imaging systems by utilizing parallel processing and reducing redundant data transmission operations, the archive-initiated method comprising:

receiving, at a long-term archive system, scheduling information from a hospital information system or EMR indicating upcoming patient examinations;

automatically analyzing, by the long-term archive system, the scheduling information to identify patients requiring access to prior medical imaging studies for clinical comparison purposes;

for each identified patient, executing, by the long-term archive system, a single coordinated database search operation across the long-term archive system to locate relevant prior studies, thereby avoiding multiple redundant search operations;

implementing a coordinated distribution process comprising:

determining target PACS by:

parsing the scheduling information, by the long-term archive system, to identify an examination location;

querying, by the long-term archive system, a PACS registry database to identify PACS associated with an ordering physician, the examination location, and an interpreting physician;

checking availability status of the target PACS;

selecting available PACS with sufficient storage capacity for the prior medical imaging studies, without requiring input from the PACS; and determining data volume and transmission time requirements for the prior medical imaging studies;

when data volume equals or exceeds a predetermined threshold, selecting multi-threaded direct file transfer using SMB/CIFS protocol to bypass DICOM processing overhead;

when data volume is below the predetermined threshold, selecting multi-threaded DICOM Send operations that eliminate resource-intensive DICOM Query components;

executing the coordinated distribution process using parallel processing to transmit multiple prior medical imaging studies simultaneously to all requiring PACS through a centralized distribution operation; and recording successful transmissions in a distribution tracking database;

wherein the coordinated distribution process improves data transmission speed by utilizing parallel processing and network performance by eliminating redundant DICOM Query/Retrieve operations that would otherwise be generated by individual PACS requesting identical data.

14. The archive-initiated method for increasing data transmission speed and optimizing network performance in medical imaging systems by utilizing parallel processing and reducing redundant data transmission operations of claim 13, wherein the predetermined threshold is adjustable to achieve optimal performance in a given environment.

15. The archive-initiated method for increasing data transmission speed and optimizing network performance in medical imaging systems by utilizing parallel processing and reducing redundant data transmission operations of claim 13, wherein implementing the coordinated distribution process further comprises:

monitoring network bandwidth utilization in real-time;

adjusting transmission schedules to avoid peak network usage periods; and implementing traffic shaping algorithms to maintain quality of service for concurrent medical imaging operations.

16. The archive-initiated method for increasing data transmission speed and optimizing network performance in medical imaging systems by utilizing parallel processing and reducing redundant data transmission operations of claim 13, further comprising:

establishing baseline archive system and network performance metrics before implementing the coordinated distribution process;

calculating an optimal number of threads to run to transmit data without causing overload to long-term archive and an enterprise network, with each thread responsible for sending one study;

measuring post-implementation network performance metrics; and calculating improvement percentages in network bandwidth utilization and transmission completion times.

17. The archive-initiated method for increasing data transmission speed and optimizing network performance in medical imaging systems by utilizing parallel processing and reducing redundant data transmission operations of claim 13, wherein analyzing the scheduling information comprises:

parsing examination type codes to determine likelihood of requiring prior study comparison;

identifying examination urgency levels to prioritize transmission operations; and correlating patient medical history data with examination types to predict prior study relevance.

18. The archive-initiated method for increasing data transmission speed and optimizing network performance in medical imaging systems by utilizing parallel processing and reducing redundant data transmission operations of claim 13, further comprising implementing a fallback mechanism wherein:

when the coordinated distribution process fails for any PACS, the long-term archive system automatically enables conventional DICOM Query/Retrieve functionality for that specific PACS; and monitoring a fallback mechanism usage to identify and resolve system performance issues.

19. The archive-initiated method for increasing data transmission speed and optimizing network performance in medical imaging systems by utilizing parallel processing and reducing redundant data transmission operations of claim 13, wherein recording successful transmissions comprises:

generating unique transaction identifiers for each distribution operation;

storing transmission timestamps, data volumes, and recipient PACS identifiers in the distribution tracking database;

implementing data retention policies that automatically purge tracking records after predetermined periods while maintaining aggregate performance statistics.

* * * * *